(12) United States Patent
Bao et al.

(10) Patent No.: US 10,723,998 B2
(45) Date of Patent: Jul. 28, 2020

(54) APPLICATION OF ETHYL P-METHOXYCINNAMATE AND DERIVATIVES THEREOF IN MAINTAINING SELF-RENEWAL AND PLURIPOTENCY OF STEM CELLS

(71) Applicant: NORTHEAST NORMAL UNIVERSITY, Chuangchun, Jilin (CN)

(72) Inventors: Yongli Bao, Jilin (CN); Yuxin Li, Jilin (CN); Hongshuang Qin, Jilin (CN)

(73) Assignee: Northeast Normal University, Changchun, Jilin (CN)

( * ) Notice: Subject to any disclaimer, the term of this patent is extended or adjusted under 35 U.S.C. 154(b) by 0 days.

(21) Appl. No.: 15/546,504

(22) PCT Filed: May 5, 2015

(86) PCT No.: PCT/CN2015/000311
§ 371 (c)(1),
(2) Date: Jul. 26, 2017

(87) PCT Pub. No.: WO2016/119085
PCT Pub. Date: Aug. 4, 2016

(65) Prior Publication Data
US 2018/0195039 A1    Jul. 12, 2018

(30) Foreign Application Priority Data
Jan. 26, 2015  (CN) .......................... 2015 1 0036595

(51) Int. Cl.
| C12N 5/00 | (2006.01) |
| C12N 5/0735 | (2010.01) |
| A61K 8/37 | (2006.01) |
| A61Q 19/00 | (2006.01) |
| A61K 31/216 | (2006.01) |
| A61P 3/06 | (2006.01) |
| A61K 31/277 | (2006.01) |
| A61K 31/7024 | (2006.01) |
| A61K 31/343 | (2006.01) |
| A61K 31/404 | (2006.01) |
| A61Q 19/08 | (2006.01) |
| A61P 17/00 | (2006.01) |
| C12N 5/074 | (2010.01) |

(52) U.S. Cl.
CPC .............. *C12N 5/0606* (2013.01); *A61K 8/37* (2013.01); *A61K 31/216* (2013.01); *A61K 31/277* (2013.01); *A61K 31/343* (2013.01); *A61K 31/404* (2013.01); *A61K 31/7024* (2013.01); *A61P 3/06* (2018.01); *A61P 17/00* (2018.01); *A61Q 19/00* (2013.01); *A61Q 19/08* (2013.01); *C12N 5/0696* (2013.01); *C12N 2501/999* (2013.01)

(58) Field of Classification Search
CPC ........................ C12N 5/0606; C12N 2501/999
See application file for complete search history.

(56) References Cited

FOREIGN PATENT DOCUMENTS
| CN | 1899280 A | 1/2007 |
| CN | 101703497 A | 5/2010 |
| WO | WO 2014136519 A1 | 9/2014 |

OTHER PUBLICATIONS

English translation of International Search Report for PCT/CN2015/000311, dated Oct. 30, 2015, 2 pages.
Liu et al., "CAPE Promotes the Expansion of Human Umbilical Cord Blood Derived Hematopoietic Stem and Progenitor Cells in Vitro," Science China: Life Sciences, vol. 57, No. 2, Feb. 28, 2014, pp. 188-194.

*Primary Examiner* — Marcia S Noble
(74) *Attorney, Agent, or Firm* — Klarquist Sparkman, LLP (57) ABSTRACT

Disclosed is a use of ethyl p-methoxycinnamate and derivatives thereof in preparing drugs, culture media, regulating agents or cosmetic and skin caring products for maintaining self-renewal and pluripotency of stem cells. The stem cells comprise adult stem cells, embryonic stem cells and induced pluripotent stem (iPS) cells. Also disclosed is a use of ethyl p-methoxycinnamate and the derivatives thereof in in-vitro amplification of stem cells and preparation of induced pluripotent stem (iPS) cells and a use of ethyl p-methoxycinnamate and the derivatives thereof in preparing drugs for treating cell deletion or injury diseases.

6 Claims, 3 Drawing Sheets
Specification includes a Sequence Listing.

APPLICATION OF ETHYL P-METHOXYCINNAMATE AND DERIVATIVES THEREOF IN MAINTAINING SELF-RENEWAL AND PLURIPOTENCY OF STEM CELLS

TECHNICAL FIELD

The present invention belongs to the technical field of biological medicine, and relates to a use of a class of small molecule compounds, i.e. ethyl p-methoxycinnamate and derivatives thereof in maintaining self-renewal and pluripotency of stem cells. The present invention also relates to a use of this class of small molecule compounds in preparing drugs for treating cell deletion or injury diseases and cosmetic and skin caring products, as well as a use of in-vitro amplification of stem cells and preparation of induced pluripotent stem (iPS) cells.

CROSS REFERENCE TO RELATED APPLICATIONS

This is the U.S. National Stage of International Application No. PCT/CN2015/000311, filed May 5, 2015, which was published in English under PCT Article 21(2), which in turn claims the benefit of Chinese Application No. 201510036595.0, filed Jan. 26, 2015.

BACKGROUND ART

Stem cells are a class of primitive cells with self-renewal capacity and multi-directional differentiation potential, including embryonic stem cells, adult stem cells and induced pluripotent stem (iPS) cells. Stem cells have a very important theoretical research significance and clinical application value. Using the embryonic stem cells to establish in vitro differentiation systems of a variety of cell types enables people to study the development process of mammals at the levels of cells and molecules; comparing gene transcription and expression of the embryonic stem cells with the stem cells and differentiated cells at different developmental stages can determine the molecular mechanism of embryo development and cell differentiation, meanwhile new genes can be discovered; the research of stem cells provides a new research means for the pharmacology, pharmacodynamics, toxicology, pharmacokinetics and the like of new drugs, overcoming the difficulty that the above experiments cannot be carried out directly in human body, meanwhile improving the effectiveness and safety of drug uses. Stem cells also have important applications in regenerative medicine, and the application of stem cells in the regenerative medicine involve all tissues and organs of human body, and also relate to most of medical problems faced by the mankind, such as cardiovascular diseases, diabetes, Parkinson's disease, cancer, Alzheimer's disease, autoimmune diseases, severe burns, spinal cord injury, hereditary diseases, osteoporosis, aging and so on.

In regenerative medicine, stem cell transplantation therapy has become an important means for the treatment of diseases, such as cell transplantation, organ transplantation and so on. Cell transplantation therapy is to transplant healthy stem cells into a patient's body, to repair or replace injured cells or tissues, so as to achieve the purpose of cure. Organ transplantation therapy takes stem cells as "seeds" to be subjected to directional induced differentiation in vitro to form desired tissues and organs, so as to replace the diseased tissues and organs. To use the stem cells in clinical treatment, first of all there must be sufficient sources, for example, the stem cells are generally required to be $1\text{-}4\times 10^6$/kg body weight for adult transfusion, while the content of the stem cells in each part of cord blood is only $1\times 10^7$ or so, therefore the current treatment is merely limited to children. The clinical application shows that the greater the input amount, the more the successful homing after transplantation, and the greater the probability of long-term rooting and reproduction. However, the stem cells in mammals have a very small number and tend to spontaneously differentiate, thus it is quite difficult to culture them in vitro for a long period of time in a large number. If the obtained rate of the stem cells can be tried to be improved during the process of in vitro isolation and culture, it will undoubtedly open up broad prospects for clinical applications of the stem cells.

Although growth factors and bioactive proteins can act as regulating drugs of stem cells, growth factors and bioactive proteins as macromolecular active substances, can intervene in the crisscross physiological processes in body, exhibit extremely complex multiple regulating functions, and are expensive and hard to have medicinal and clinical therapeutic value. Therefore, the potential of small molecule compounds as stem cell regulating drugs has been increasingly attached significance to by people. The small molecule compounds as drugs or culture medium additives have their unique advantages: the small molecule compounds are easy to administrate, and also easy to withdraw after physiological functions are recovered; the small molecule compounds are easy to artificially synthesize and achieve industrialized production, and have a good prospect of medicinal use; the small molecule compounds, especially natural small molecule compounds, having undergone biological metabolic processes, possess good biocompatibility, especially fewer toxic and side effects. Therefore, to search for small molecule compound regulating agents for stem cells has become a research focus of stem cell drugs.

SEQUENCE LISTING

The nucleic acid sequences listed in the accompanying sequence listing are shown using standard abbreviations for nucleotide bases, as defined by 37 C.F.R. § 1.822. Only one strand of each nucleic acid sequence is shown, but the complementary strand is understood as included by reference to the displayed strand. The Sequence Listing is submitted as an ASCII text file, created on Aug. 13, 2019, and is incorporated by reference herein.

SEQ ID NO. 1 is an upstream primer 5'-CTCGAACCA-CATCCTTCTCT-3'.

SEQ ID NO. 2 is a downstream primer 5'-TCGTGCGT-GACATTAAGGAG-3.

DISCLOSURE OF THE INVENTION

An object of the present invention is to provide a class of small molecule compounds, namely, ethyl p-methoxycinnamate and derivatives thereof, having the effect of maintaining self-renewal and pluripotency of stem cells.

The present invention is specifically realized through the following technical solution:

The present invention provides a use of ethyl p-methoxycinnamate and derivatives thereof in preparing drugs, culture media, regulating agents in maintaining self-renewal and pluripotency of stem cells.

The general structural formula of the ethyl p-methoxycinnamate and the derivatives thereof is as follows:

wherein $R_1$ is 4-OCH$_3$, $R_2$ is H, $R_3$ is H, and $R_4$ is —CH$_2$CH$_3$;

or $R_1$ is 4-OCH$_3$, $R_2$ is H, $R_3$ is H, and $R_4$ is —CH$_2$CH$_2$CH(CH$_3$)CH$_3$;

or $R_1$ is 4-OCH$_3$, $R_2$ is H, $R_3$ is COOCH$_2$CH$_3$, and $R_4$ is —CH$_2$CH$_3$;

or $R_1$ is 4-OCH$_3$, $R_2$ is H, $R_3$ is COCH$_3$, and $R_4$ is —CH$_2$CH$_3$;

or $R_1$ is 4-OCH$_3$, $R_2$ is H, $R_3$ is CN, and $R_4$ is —CH$_2$CH$_3$;

or $R_1$ is 4-OCH$_3$, $R_2$ is CH$_3$, $R_3$ is H, and $R_4$ is —CH$_2$CH(CH$_2$CH$_3$)CH$_2$CH$_2$CH$_3$;

or $R_1$ is 3,4-OCH$_3$, $R_2$ is H, $R_3$ is COCH$_2$CH$_3$, $R_4$ is —CH$_2$CH$_3$;

or $R_1$ is 3,4-OCH$_3$, $R_2$ is H, $R_3$ is CN, and $R_4$ is —CH$_2$CH$_3$;

or $R_1$ is 2,4-OCH$_3$, $R_2$ is H, $R_3$ is CN, and $R_4$ is —CH$_2$CH$_3$;

or $R_1$ is 3,4,5-OCH$_3$, $R_2$ is CH$_3$, $R_3$ is H, and $R_4$ is —CH$_2$CH$_3$;

or $R_1$ is 2-OCH$_2$CH$_3$, $R_2$ is H, $R_3$ is H, and $R_4$ is —CH$_2$CH$_3$;

or $R_1$ is 4-OCH$_2$CH$_3$, $R_2$ is H, $R_3$ is H, and $R_4$ is —CH$_2$CH$_3$;

or $R_1$ is 4-OCH$_2$CH$_2$CH$_2$CH$_3$, $R_2$ is H, $R_3$ is CN, and $R_4$ is —CH$_2$CH$_3$;

or $R_1$ is 3-COOCH$_3$, $R_2$ is H, $R_3$ is H, and $R_4$ is —CH$_2$CH$_3$;

or $R_1$ is 2-CH$_3$-5-COOCH$_3$, $R_2$ is H, $R_3$ is H, and $R_4$ is —CH$_2$CH$_3$;

or $R_1$ is 4-OCOCH$_3$, $R_2$ is H, $R_3$ is COCH$_2$CH$_3$, and $R_4$ is —CH$_2$CH$_3$;

or $R_1$ is 3-OCH$_3$-4-OCH$_2$COOCH$_2$CH$_3$, $R_2$ is H, $R_3$ is H, and $R_4$ is —CH$_2$CH$_3$;

or $R_1$ is 2-OH, $R_2$ is H, $R_3$ is H, and $R_4$ is —CH$_2$CH$_3$;

or $R_1$ is 3,4-OH, $R_2$ is H, $R_3$ is H, and $R_4$ is —CH$_2$CHC(CH$_3$)CH$_3$;

or $R_1$ is 3,4-OH, $R_2$ is H, $R_3$ is H, and $R_4$ is —CH$_2$CH$_2$C$_6$H$_5$;

or $R_1$ is 3,4-OH, $R_2$ is H, $R_3$ is H, and $R_4$ is or $R_1$ is 3,4-OH, $R_2$ is H, $R_3$ is H, and $R_4$ is or $R_1$ is H, $R_2$ is H, $R_3$ is H, and $R_4$ is —CH$_2$CH$_3$;

or $R_1$ is H, $R_2$ is H, $R_3$ is H, and $R_4$ is —CH(CH$_3$)CH$_3$;

or $R_1$ is H, $R_2$ is H, $R_3$ is H, and $R_4$ is —CH$_2$CH$_2$CH$_2$CH$_3$;

or $R_1$ is H, $R_2$ is H, $R_3$ is H, and $R_4$ is —CH$_2$CH(CH$_3$)CH$_3$;

or $R_1$ is H, $R_2$ is H, $R_3$ is H, and $R_4$ is —CH(CH$_3$)CH$_2$CH$_3$;

or $R_1$ is H, $R_2$ is H, $R_3$ is H, and $R_4$ is —CH$_2$CH$_2$CH(CH$_3$)CH$_3$;

or $R_1$ is H, $R_2$ is H, $R_3$ is H, and $R_4$ is —CH$_2$CH$_2$CH$_2$OOCCH=CHC$_6$H$_5$;

or $R_1$ is H, $R_2$ is H, $R_3$ is H, and $R_4$ is —CH$_2$CH$_2$C$_6$H$_5$;

or $R_1$ is H, $R_2$ is H, $R_3$ is H, and $R_4$ is —CH$_2$CH(CH$_3$)C$_6$H$_5$;

or $R_1$ is H, $R_2$ is H, $R_3$ is CN, and $R_4$ is —CH$_2$CH$_3$;

or $R_1$ is H, $R_2$ is CH$_3$, $R_3$ is H, and $R_4$ is —CH$_2$CH$_3$;

or $R_1$ is H, $R_2$ is C$_6$H$_5$, $R_3$ is CN, and $R_4$ is —CH$_2$CH$_3$;

or $R_1$ is 2,6-Cl, $R_2$ is H, $R_3$ is H, and $R_4$ is —CH$_2$CH$_3$;

or $R_1$ is 4-Br, $R_2$ is H, $R_3$ is H, and $R_4$ is —CH$_2$CH$_3$;

or $R_1$ is 2-CF$_3$, $R_2$ is H, $R_3$ is H, and $R_4$ is —CH$_2$CH$_3$;

or $R_1$ is 2-OH-4-Br, $R_2$ is H, $R_3$ is H, and $R_4$ is —CH$_2$CH$_3$;

or $R_1$ is 4-Cl, $R_2$ is H, $R_3$ is COOCH$_2$CH$_3$, and $R_4$ is —CH$_2$CH$_3$;

or $R_1$ is 4-Cl, $R_2$ is H, $R_3$ is OCH$_2$CH$_3$, and $R_4$ is —CH$_2$CH$_3$;

or $R_1$ is 3,4-F, $R_2$ is H, $R_3$ is OCH$_2$CH$_3$, and $R_4$ is —CH$_2$CH$_3$;

or $R_1$ is 2-Cl-4-F, $R_2$ is H, $R_3$ is CN, and $R_4$ is —CH$_2$CH$_3$;

or $R_1$ is 3-Cl-4-OCH$_3$, $R_2$ is H, $R_3$ is CN, and $R_4$ is —CH$_2$CH$_3$;

or $R_1$ is 2-Cl-4-OCH$_3$, $R_2$ is H, $R_3$ is CN, and $R_4$ is —CH$_2$CH$_3$;

or $R_1$ is 4-NH$_2$, $R_2$ is H, $R_3$ is H, and $R_4$ is —CH$_2$CH$_3$;

or $R_1$ is 3-CN, $R_2$ is H, $R_3$ is H, and $R_4$ is —CH$_2$CH$_3$;

or $R_1$ is 4-NO$_2$, $R_2$ is H, $R_3$ is H, and $R_4$ is —CH$_2$CH$_3$;

or $R_1$ is 4-(2,4-F—C$_6$H$_4$), $R_2$ is CH$_3$, $R_3$ is H, and $R_4$ is —CH$_2$CH$_3$;

or $R_1$ is 4-OCH$_3$, $R_2$ is H, $R_3$ is H, and $R_4$ is —CH$_2$—C$_6$H$_4$—CH$_2$—OOC—CH=CH—C$_6$H$_4$—O—CH$_3$;

or $R_1$ is 4-OCH$_3$, $R_2$ is H, $R_3$ is H, and $R_4$ is —CH$_2$—C—CH$_2$—OOC—CH=CH—C$_6$H$_4$—O—CH$_3$;

or $R_1$, $R_2$ and $R_3$ form a heterocyclic structure and $R_4$ is —CH$_2$CH$_3$;

or $R_1$, $R_2$ and $R_3$ form a heterocyclic structure and R$_4$ is —CH$_2$CH$_3$;
or R$_1$, R$_2$ and R$_3$ form a heterocyclic structure and R$_4$ is —CH$_2$CH$_3$;
or R$_1$, R$_2$ and R$_3$ form a heterocyclic structure and R$_4$ is —CH$_2$CH$_3$;
or R$_1$ is —N—CH$_3$(CH$_3$), R$_2$ is H, and R$_3$ and R$_4$ form a heterocyclic structure The ethyl p-methoxycinnamate and the derivatives thereof include: ethyl p-methoxycinnamate and the derivatives thereof include: ethyl p-methoxycinnamate, iso-pentyl methoxycinnamate, diethyl 4-methoxybenzalmalonate, ethyl 2-(4-methoxybenzylidene)acetoacetate, ethyl 2-cyano-3-(4-hydroxyethylphenyl)acrylate, octyl 4-methoxycinnamate, diethyl 2-(3,4-dimethoxybenzylidene)malonate, ethyl 2-cyano-3-(3,4-dimethoxyphenyl)-2-butenoate, ethyl trans-2-cyano-3-(2,4-dimethoxyphenyl)-2-acrylate, ethyl trans-3-(3,4,5-trimethoxyphenyl)-2-crotonate, ethyl 2-hydroxyethylcinnamate, ethyl trans-4-ethoxycinnamate, ethyl 3-(4-butoxyphenyl)-2-cyanoacrylate, methyl 3-(trans-3-hydroxyethyl-3-oxo-1-propenyl)benzoate, methyl 3-(trans-3-ethoxy-3-oxo-1-propenyl)-4-methylbenzoate, diethyl 4-acetoxybenzylidenemalonate, ethyl 3-(3-methoxy-4-methoxycarbonylmethoxyphenyl)acrylate, ethyl trans-2-hydroxycinnamate, caffeic acid-1,1-dimethylacrylate, trans-caffeic acid-1-phenylethyl ester, neochlorogenic acid, chlorogenic acid, ethyl cinnamate, iso-propyl cinnamate, butyl cinnamate, iso-butyl cinnamate, propyl 3-methylcinnamate, iso-pentyl cinnamate, 3-cinnamoyloxypropyl 3-propylacrylate, phenylethyl cinnamate, 3-phenylpropyl cinnamate, ethyl trans-2-cyanocinnamate, ethyl trans-β-methylcinnamate, ethyl 2-cyano-3,3-diphenylacrylate, ethyl 2,6-dichlorocinnamate, ethyl trans-4-bromo cinnamate, ethyl trans-3-(2-trifluoromethylphenyl)-2-acrylate, ethyl trans-3-(4-bromo-2-hydroxyphenyl)-2-acrylate, diethyl 4-chlorobenzylidenemalonate, ethyl cis-3-(4-chlorophenyl)-2-hydroxyethyl-2-acrylate, ethyl cis-3-(3,4-difluorophenyl)-2-ethoxy-2-acrylate, ethyl 3-(2-chloro-4-fluorophenyl)-2-cyano-2-acrylate, ethyl 3-(3-chloro-4-methoxyphenyl)-2-cyanoacrylate, ethyl 3-(2-chloro-4-methoxyphenyl)-2-cyanoacrylate, ethyl 4-aminocinnamate, ethyl 3-cyanocinnamate, ethyl 4-nitrocinnamate, 3-[2,4-difluoro (1,1-biphenyl)-4-yl]-2-butenoate, 3-[3-(4-methoxyphenyl) acryloyloxymethyl]benzyl 3-(4-methoxyphenyl)acrylate, 4-[3-(4-methoxyphenyl)acryloyloxy]butyl-2-ynyl 3-(4-methoxyphenyl)acrylate, ethyl indole-2-carboxylate, ethyl 6-methoxy-1-benzofuran-2-carboxylate, ethyl 6-amino-3-methyl-1-benzofuran-2-carboxylate, ethyl 5-methylindole-2-carboxylate, and trans-3-(4-dimethylaminobenzylidene) dihydro-2(3H)-furanone.

The stem cells of the present invention comprise adult stem cells, embryonic stem cells or induced pluripotent stem (iPS) cells.

The ethyl p-methoxycinnamate and the derivatives thereof maintain self-renewal capacity and pluripotent state of the stem cells by promoting expression of Oct4 genes.

The pharmaceutical composition of the present invention comprises a therapeutically effective amount of the ethyl p-methoxycinnamate and derivatives thereof and a pharmaceutically acceptable carrier, and the carrier is solvent, dispersant, coating, antibacterial and antifungal agent, isotonic agent and absorption delaying agent.

The drugs of the present invention can be diluted by a user before use or used directly, and preparation thereof can be conducted by a general processing method commonly known by the person ordinarily skilled in the art.

The drugs of the present invention can be prepared into pharmaceutical dosage forms suitable for different administration routes, wherein preferable dosage forms are capsule and tablet. The capsule can comprise any standard pharmaceutically acceptable substances such as gelatin or cellulose. The tablet can be prepared by compressing a pharmaceutical composition with a solid phase carrier and a lubricant in a conventional manner. The solid phase carrier includes starch and sugar bentonite.

The pharmaceutical composition of the present invention also can be administrated through parenteral routes. Administration dosage forms for parenteral routes include aqueous solution, isotonic saline solution or 5% sugar solution of the pharmaceutical composition of the present invention and other formulations formed with other pharmaceutically acceptable excipients known in the art.

A dosage range of formulation of the drugs of the ethyl p-methoxycinnamate and the derivatives thereof of the present invention for maintaining self-renewal capacity and pluripotent state of the stem cells is 0.01~100 mg/kg.

A use of ethyl p-methoxycinnamate and the derivatives thereof of the present invention in in-vitro large-scale preparation of stem cells, which is specifically the use in in-vitro amplification of stem cells and preparation of induced pluripotent stem (iPS) cells.

The present invention further provides a use of ethyl p-methoxycinnamate and the derivatives thereof in preparing drugs for treating cell deletion or injury diseases. The injury diseases are injury diseases of cells, tissues or organs, specifically nervous system diseases, immune system diseases, blood system diseases, cardiovascular diseases or skin diseases.

The present invention further provides a use of ethyl p-methoxycinnamate and the derivatives thereof in preparing cosmetic and skin caring products.

Ethyl p-methoxycinnamate and the derivatives thereof of the present invention can be suspended in a pharmaceutically acceptable carrier (such as a physiological solution), and administered orally or by intravenous infusion, or by subcutaneous, submuscular, intrathoracic, intraperitoneal, intrarectal, intravaginal, intranasal, intragastric, intratracheal, intrapulmonic injection or infusion and so on.

Ethyl p-methoxycinnamate and the derivatives thereof of the present invention can be suspended in the cosmetic and skin caring products, and achieve the efficacy of activating skin stem cells by means of applying.

Ethyl p-methoxycinnamate and the derivatives thereof of the present invention can be directly added to a cell culture solution for amplification of stem cells in vitro.

Beneficial effects of the present invention are as follows: by studying the small molecule compounds, it is discovered that ethyl p-methoxycinnamate and the derivatives thereof can promote expression of Oct4 genes, so as to maintain the self-renewal capacity and the pluripotent state of stem cells, and they can act as regulating drugs or culture medium additives for maintaining the self-renewal and pluripotency of stem cells, and provide a large number of stem cells for clinical transplantation, and provide a new perspective and a new idea for the treatment of cell loss or injury diseases.

DETAILED DESCRIPTION OF EMBODIMENTS

Below the present invention is further described in conjunction with examples. The following description is merely directed to preferable examples of the present invention, rather than limits the present invention in other forms, and any person skilled in the art may utilize the technical contents disclosed above and modify them into equivalent examples. Any simple modifications or equivalent variations made to the following examples according to the technical essence of the present invention, without departing from the contents of the solutions of the present invention, should fall within the scope of protection of the present invention.

Example 1 Effect of Ethyl p-Methoxycinnamate on Oct4 Promoter Activity

According to a method described in literature (Yang H M, Do H J, Oh J H, et al. Characterization of putative cis-regulatory elements that control the transcriptional activity of the human Oct4 promoter[J]. Journal of cellular biochemistry, 2005, 96(4):821-830), the promoter of Oct4 gene was picked and cloned into pGL3-Basic, so as to construct pGL3-Oct4P-Basic reporter plasmid. One day before transfection, mouse teratoma cells P19 were inoculated into a 6-well cell culture plate at a density of $2 \times 10^5$ cells/well to make the cells grown to about 80% before transfection. A liposomal transfection reagent Entranster™-D from Engreen company was used to perform the transfection according to the instructions. The P19 cells were transfected with the target plasmid pGL3-Oct4P-Basic, and the total amount of the plasmid used for the transfection was 3 μg/well. The plasmid was added to 50 μL of serum-free DMEM culture medium and fully mixed. 9 μL of the transfection reagent was then added to another 50 μL of the serum-free DMEM culture medium, mixed well, and the mixture allowed to stand for 5 min. The DMEM culture medium containing the transfection reagent was then added to the DMEM culture medium containing the plasmid, and the mixture was immediately pipetted more than 10 times, and allowed to stand at room temperature for 30 min. 900 μL of DMEM culture medium containing 10% fetal calf serum were added to the mixed solution, and gently mixed well. The original cell culture medium in the 6-well plate was discarded, and was replaced by the above mixed solution. The cells were re-suspended in the DMEM culture medium containing 10% fetal calf serum after being cultured for 4-6 h in a 5% $CO_2$ cell incubator at 37° C. The above cells were inoculated in a 96-well plate at a density of $8 \times 10^3$ cells/well. After being cultured for 24 h, the culture medium was absorbed and removed, the DMEM culture medium containing 3% fetal calf serum was added, and the drug to be screened was added to the culture medium to result in a final concentration of 5 μg/mL, meanwhile DMSO was used as a control. After subsequent continuous culture for 12-24 h, the cells were lysed, and luciferase activity was assayed.

Figure 1:
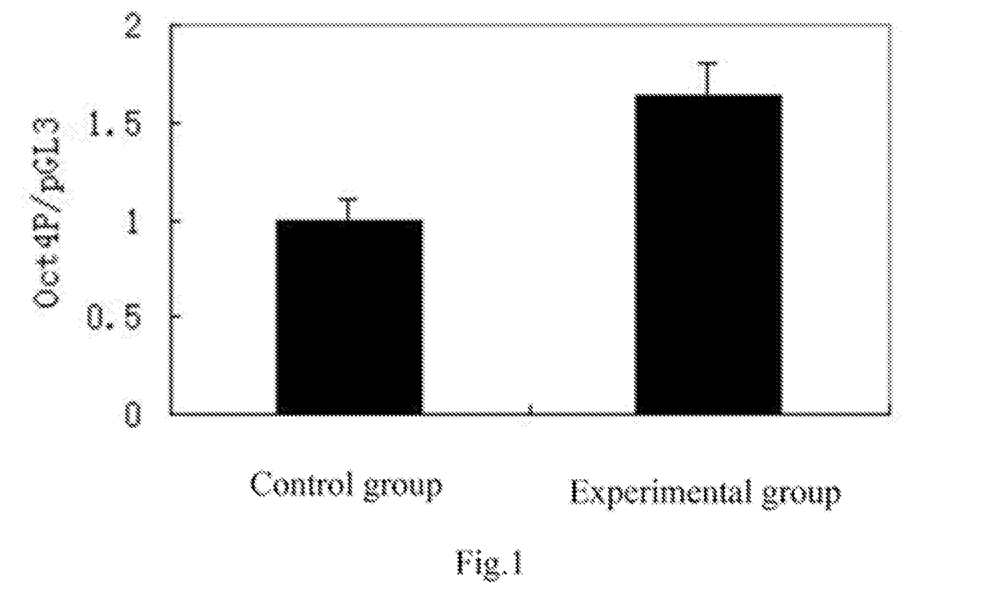
FIG. 1 shows the effect of ethyl p-methoxycinnamate on the activity of Oct4 promoter.

Luciferase Reporter Assay System and FluoStar Optima were used to assay the luciferase activity of the transfected cell lysis solution. To 45 μL of the cell lysis solution was added 5 μL of Assay Cocktail reagent, after they were mixed well, 100 μL of Luciferin reaction solution was added, and fluorescence counting in 2 s was measured using FluoStar Optima instrument, which reflected the activity level of the studied plasmid reporter genes expressing firefly luciferase. To another 20 μL of the cell lysis solution was added 37.5 μL of β-gal Buffer, followed by 12.5 μL of ONPG (6 mg/mL), and after they were mixed well, they were allowed to stand at 37° C. for 30 min. An absorption value at 450 nm was assayed using a microplate reader, which reflected the activity level of internal reference plasmid pCMV-β-gal expressing β-galactosidase. The ratio between the activity of the firefly luciferase and the activity of the β-galactosidase (β-gal) excluded the difference of the sample transfection efficiency, and could relatively objectively reflect the difference of promoter activity between samples. The relative luciferase activity of different samples was calculated through the following equation:

$$\text{Relative luciferase activity} = \frac{\text{Firefly luciferase activity of each sample}}{\beta\text{-galactosidase activity of each sample}}$$

Results are as shown in FIG. 1. The effect of ethyl p-methoxycinnamate on the activity of Oct4 promoter reached a statistically significant difference (*p<0.05).

Example 2 Effect of Ethyl p-Methoxycinnamate on the Expression of Oct4 mRNA

1) mRNA Extraction and Reverse Transcription

P19 cells were inoculated in a 6-well cell culture plate at a density of $2 \times 10^5$ cells/well. After 24 h, DMEM culture medium containing 3% serum were used for replacement. Ethyl p-methoxycinnamate was added to the experimental group to render its final concentration at 5 μg/mL, and a control group was treated with DMSO. After 12 h, the 6-well plate overgrown with monolayer cells was taken out from a cell incubator, and the cells were washed 3 times with pre-cooled PBS. 1 mL of a pre-cooled Trizol solution was added. After vigorous pipetting, the mixture was transferred to an EP tube and allowed to stand at room temperature for 5 min. Then 200 μL of chloroform was added to the mixture, vigorously mixed well for 15 s, and the mixture containing chloroform was allowed to stand at room temperature for 2 min and centrifuged at 12000 rpm at 4° C. for 15 min. An upper aqueous phase was pipetted into another EP tube, and an equal volume of pre-cooled isopropanol was added, and the mixture was inverted several times and allowed to stand at room temperature for 10 min to precipitate RNA. After centrifugation at 12000 rpm for 10 min, the supernatant was discarded, and to the precipitate was added 1 mL of 75% ethanol (prepared by 0.1% DEPC water) for washing, followed by centrifugation at 7500 rpm for 5 min (this step was repeated once). The supernatant was discarded. After natural drying (or oven drying at 37° C.), an appropriate amount of 0.1% DEPC water was added for dissolving at 37° C. for 30 min (or dissolving at 55° C. for 10 min), and the dissolved RNA was stored at −80° C. for standby use.

Reverse transcription was performed using a Reverse Transcription System kit from TaKaRa company, and the reaction system was as follows:

| | |
|---|---|
| RNA template | 1 μg |
| 5× Reverse Transcription Buffer | 4 μL |
| 10 mM dNTP mixture | 2 μL |
| RNase inhibitor | 20M (0.5 μL) |
| Oligo (dT) 15 primer | 50 pmol (1 μL) |
| AMV RTase | 5M (2 μL) |
| 0.1% DEPC H$_2$O | Added to 20 μL |

Firstly, the RNA template, 0.1% DEPC water and Oligo (dT) 15 primer were added to a clean EP tube, for water bath at 70° C. for 2 min followed by centrifugation at 1000 rpm for 1 min. The other components of the reverse transcription were added to the EP tube, for water bath at 42° C. for 1 h. The reaction was stopped at 70° C. for 8 min, and finally 0.1% DEPC water was added to the EP tube, until the volume of the solution in the EP tube was 100 μL.

2) RT-PCR Reaction

Upstream primer: 5'-CTCGAACCACATCCTTCTCT-3', SEQ ID NO. 1: downstream primer: 5'-TCGTGCGTGACATTAAGGAG-3, SEQ ID NO. 2.

PCR Reaction System (25 μL):

| | |
|---|---|
| Template DNA (1 μg/μL) | 5 μL |
| Upstream primer (10 μM) | 1 μL |
| Downstream primer (10 μM) | 1 μL |
| 10× Taq Buffer | 2.5 μL |
| 2.5 mM dNTP | 2 μL |
| Taq DNA polymerase | 1 μL |
| Sterile water | Added water to 25 μL |

PCR Reaction Conditions:

94° C., 5 min

94° C., 40 s ⎫
52° C., 40 s ⎬ 25 cycles
72° C., 1 min ⎭

72° C., 8 min

3) Agarose Gel Electrophoresis 0.4 g of agarose was weighed and placed in a conical flask. 40 mL of 1×TAE electrophoresis buffer was added to it, and the mixture was placed in a microwave oven to heat until all the agarose melted, and the resulting mixture was taken out and shaken well. This process was repeated three times. When the solution was cooled to about 50° C., 20 μL of anthocyanin dye was added, so that the final concentration of anthocyanin dye was 0.5 mg/mL, and the mixture was mixed well. An electrophoresis gel solution was poured into a tank, allowed to stand cool down, and solidified for 30 min. After the gel completely solidified, the comb was pulled out, 1×TAE electrophoresis buffer was poured into the electrophoresis tank until the liquid level was just over the upper surface of a gel plate. PCR products were added to a 10× gel loading buffer in proportion, mixed well, and the resulting mixture was carefully added to sample wells using a micropipettor. After loading, the electrophoresis tank cover was closed, and the power was turned on, so that the voltage was maintained at 100-140 V. When a bromophenol blue band moved to about 2 cm from the gel front, the electrophoresis was stopped, and a gel imaging system was used for observing and photographing.

Figure 2:
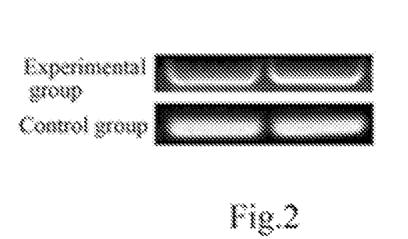
FIG. 2 shows the effect of ethyl p-methoxycinnamate on the expression of Oct4 mRNA.

Results are as shown in FIG. 2. Ethyl p-methoxycinnamate can significantly promote the expression of Oct4 mRNA.

Example 3 Effect of Ethyl p-Methoxycinnamate on Oct4 Protein Expression

The effect of ethyl p-methoxycinnamate on Oct4 protein expression was assayed using a Western Blot method. Mouse teratoma cells P19 were inoculated in a 6-well plate. After 24 h, ethyl p-methoxycinnamate with a final concentration of 5 μg/mL was added to continue to act for another 24 h, and the control group was treated with DMSO. After the cells were washed with PBS three times, the cells were scraped with a scraper, transferred to an EP tube, and centrifuged at 4000 rpm for 5 min. The supernatant was discarded. 90 μL of lysis solution (50 mM Tris-HCl pH 7.5, 150 mM NaCl, 1 mM NaF, 0.5% NP-40, 2 μg/mL Aprotinin, and 1 mM PMSF) was added to each tube of precipitate, and the EP tube was treated on ice for 30 min and vortexed once every 5 min, so that the cells were completely lysed. After centrifugation at 12000 rpm for 10 min, the supernatant was transferred to a new EP tube, 1/3 volume of 4× protein loading buffer was added, mixed well, and boiled for 10 min, and after instantaneous centrifugation, the mixture was subjected to electrophoresis or placed at −80° C. to be frozen for standby use.

A transfer membrane buffer was prepared and precooled at 4° C. A PVDF membrane was soaked in methanol for 40 s, then taken out and soaked in the transfer membrane buffer for standby use. The transfer membrane buffer was placed in a square plate, and a transfer membrane device was installed under the liquid surface. The transfer membrane device was placed in an electrophoresis tank, and the transfer membrane buffer was poured into the electrophoresis tank. The PVDF membrane was taken out after membrane transfer at 100 V for 2 h, and positive and negative surfaces of the membrane and the electrophoretic direction were marked. The PVDF membrane was washed with TBST (0.2% Tween 20), once every 5 min, and twice in total, and blocked with 5% skim milk powder at room temperature for 2 h. After that, the PVDF membrane was washed twice with TBST (0.2% Tween 20), 5 min each time (the membrane washing was conducted on a shaker, the same below). Antibodies of Oct4, after being diluted with TBST (0.2% Tween 20) at 1:500, was placed in a hybridization bag together with the PVDF membrane to stay overnight at 4° C. The PVDF membrane was taken out and rapidly washed with TBST (0.2% Tween 20) twice, and then washed twice for 5 min, and 3 times for 15 min. HRP-goat anti-mouse secondary antibody (0.8 mg/mL), after being diluted with TBST (0.2% Tween 20) at 1:2000, was placed in a hybridization bag together with the PVDF membrane, to incubate at room temperature for 40 min on the shaker. The PVDF membrane was taken out, and rapidly washed twice with TBST (0.2% Tween 20), and then washed twice for 5 min, and 3 times for 15 min. The PVDF membrane was subjected to ECL color development.

Figure 3:
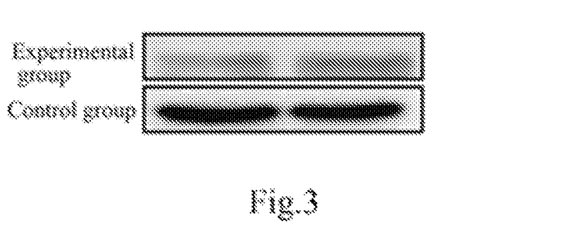
FIG. 3 shows the effect of ethyl p-methoxycinnamate on the expression of Oct4 protein.

Results are as shown in FIG. 3. Ethyl p-methoxycinnamate can promote the expression of Oct4 protein.

Example 4 Ethyl p-Methoxycinnamate and Derivatives Thereof Promote the Formation of Microspheres of Suspendedly Cultured Stem Cells 5 g agar was weighed and placed in a flask, then 100 mL of ultra-pure water was added, and the mixture was mixed well, sealed, and then autoclaved for 30 min. In a super clean bench, 9 mL of pre-heated (50-60° C.) serum-free DMEM culture medium was pipetted into a 10 mL centrifuge tube, then 1 mL of uncooled 5% agar was added, and rapidly mixed well with a pipette, resulting in 0.5% agar. 1 mL of 0.5% agar was pipetted into one well of a 6-well plate and cooled at room temperature for 20-30 min, resulting in a 0.5% soft agar culture medium.

In the super clean bench, D-Hanks was gently added to the surface of the soft agar culture medium, and the D-Hanks was discarded after being gently shaken 2 to 3 times. Cleaning was repeated once. The mouse teratoma cells P19 were gently inoculated on the surface of the soft agar culture medium at a cell density of $4 \times 10^5$ cells/well. After the cell inoculation, ethyl p-methoxycinnamate was added to 1 mL of DMEM culture medium containing 10% fetal calf serum, mixed well, and then gently added to the experimental group. A final concentration of ethyl p-methoxycinnamate was 5 μg/mL. The control group was treated with DMSO. The next day, half the amount of the solution was changed, through a method that 1 mL of the culture medium were gently absorbed from one side of the well (note that the cells should not be absorbed), and then fresh culture medium were added, and ethyl p-methoxycinnamate was added thereto, so that the final concentration of the fresh culture medium was 5 μg/mL. After 7 d, 200 μL MTT (5 mg/mL) was added to the control group and the experimental group respectively, and both of them were placed back into an incubator for continuous culture for 4 h. After successful dyeing, the cells were photographed.

Figure 4:
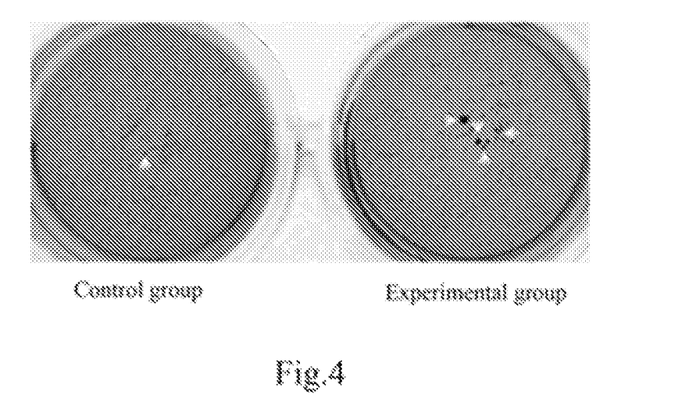
FIG. 4 shows the effect of ethyl p-methoxycinnamate on the formation of microspheres of suspendedly cultured stem cells.

Results are as shown in FIG. 4. Compared with the control group, in the experimental group, the P19 cells can form a higher amount of larger and more typical microspheres. It indicates that ethyl p-methoxycinnamate has the effect of maintaining the self-renewal and pluripotency of stem cells.

Example 5 Ethyl p-Methoxycinnamate Promotes Formation of Microspheres of Adherently Cultured Stem Cells In a super clean bench, mouse teratoma cells P19 were inoculated in a 6-well plate at a density of $1 \times 10^4$ cells/well, and DMEM culture medium containing 10% fetal calf serum was added to result in a final volume of 2 mL. The cell culture plate was gently shaken, so that the cells were uniformly distributed in the cell culture plate, and then placed in a cell incubator to be cultured. After 24 h, the old culture medium were discarded, and 3% fetal calf serum DMEM culture medium containing ethyl p-methoxycinnamate was added, so that the final concentration of ethyl p-methoxycinnamate was 5 μg/mL. The original culture medium was discarded every 24 h, and fresh DMEM culture medium containing 3% fetal calf serum was added, and the final concentration of ethyl p-methoxycinnamate therein was made to be 5 μg/mL likewise. After continuous culture of 22 d, the cells were photographed.

Figure 5:
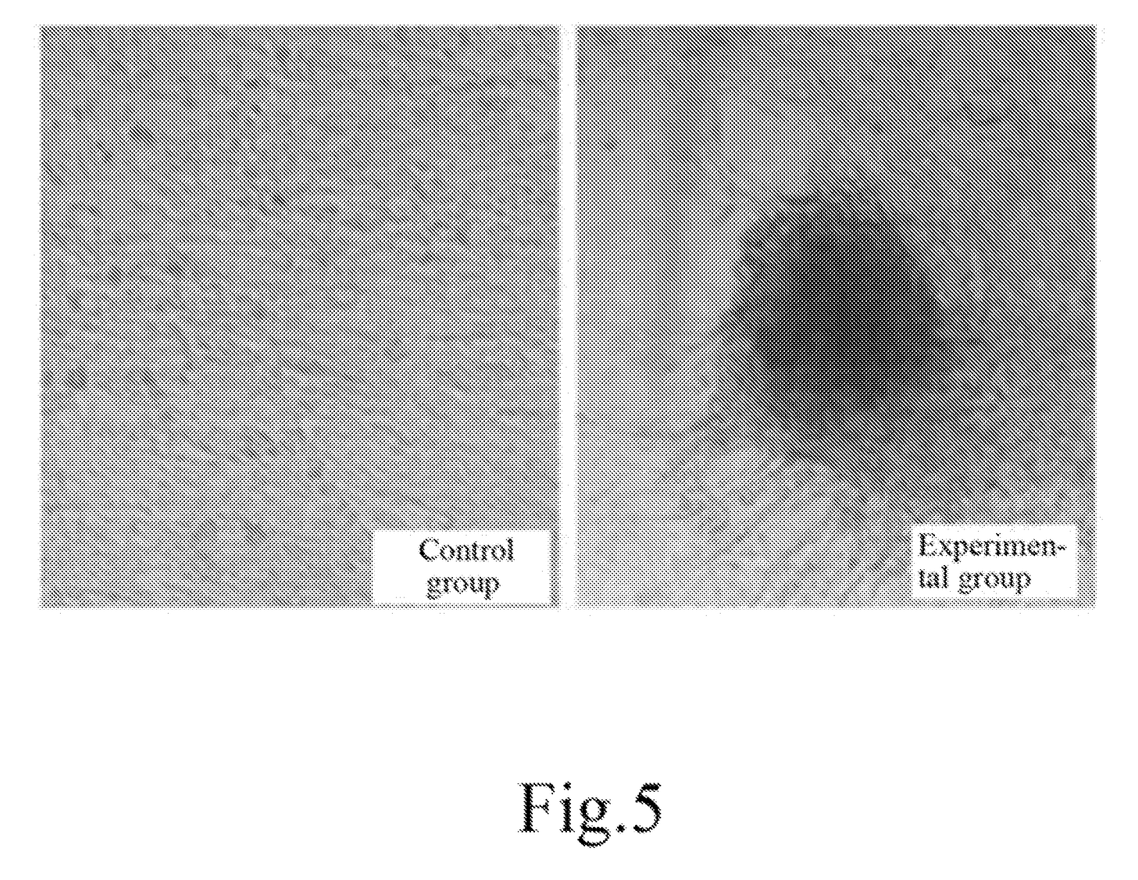
FIG. 5 shows the effect of ethyl p-methoxycinnamate on the formation of microspheres of adherently cultured stem cells.

Results are as shown in FIG. 5. The control group cannot form microspheres, but in the experimental group, the P19 cells can form typical microspheres. It indicates that ethyl p-methoxycinnamate has the effect of maintaining the self-renewal and pluripotency of stem cells again.

Example 6 Derivatives of Ethyl p-Methoxycinnamate can Promote Expression of Oct4

The effect of derivatives of ethyl p-methoxycinnamate on Oct4 expression was assayed by a luciferase reporter gene method, the derivatives including diethyl 4-methoxybenzalmalonate, ethyl 3-(3-methoxy-4-methoxycarbonylmethoxyphenyl)acrylate, diethyl 4-acetoxybenzylidenemalonate, chlorogenic acid, ethyl cinnamate, 3-cinnamoyloxypropyl 3-propylacrylate, ethyl 2-cyano-3,3-diphenylacrylate, ethyl 2,6-dichlorocinnamate, diethyl 4-chlorobenzylidenemalonate, ethyl 4-aminocinnate, ethyl 3-cyanocinnamate, ethyl 4-nitrocinnamate, 3-[3-(4-methoxyphenyl)acryloyloxymethyl]benzyl 3-(4-methoxyphenyl)acrylate, 4-[3-(4-methoxyphenyl)acryloyloxy]butyl-2-ynyl 3-(4-methoxyphenyl)acrylate, ethyl indole-2-carboxylate, and ethyl 6-methoxy-1-benzofuran-2-carboxylate.

One day before transfection, mouse teratoma cells P19 were inoculated into a 24-well cell culture plate at a density of $1 \times 10^5$ cells/well, to make the cells grown to about 80% before transfection. A liposomal transfection reagent Entranster™-D from Engreen company was used to perform the transfection according to the instructions, to co-transfect the P19 cells with target plasmid (PGL3-Oct4P-Basic or pGL3-Basic) and reference plasmid (pCMV-β-gal). The total amount of the plasmid used for transfection was 1 μg/well (the target plasmid:the reference plasmid=2:1). The plasmid was added to 25 μL of serum-free DMEM culture medium, and fully mixed. 3 μL of the transfection reagent was then added to another 25 μL of serum-free DMEM culture medium, mixed well, and allowed to stand for 5 min. The DMEM culture medium containing the transfection reagent was then added to the DMEM culture medium containing the plasmid, and the mixture was immediately pipetted more than 10 times, and allowed to stand at room temperature for 30 min. 250 μL of DMEM culture medium containing 10% fetal calf serum was added to the mixed solution, and gently mixed well. The original cell culture medium in the 24-well plate was discarded, and replaced with the above mixed solution. After being cultured for 4-6 h in a 5% $CO_2$ cell incubator at 37° C., the original culture medium was absorbed and removed, and replaced with 500 μL of DMEM culture medium containing 10% fetal calf serum. After being cultured for 24-36 h, the culture medium was absorbed and removed, the DMEM culture medium containing 3% fetal calf serum was added, and ethyl p-methoxycinnamate was added to the culture medium, to result in a final concentration of 5 μg/mL, meanwhile DMSO was used as a control. After subsequent continuous culture for 12-24 h, the cells were lysed, and the luciferase activity was assayed.

Figure 6:
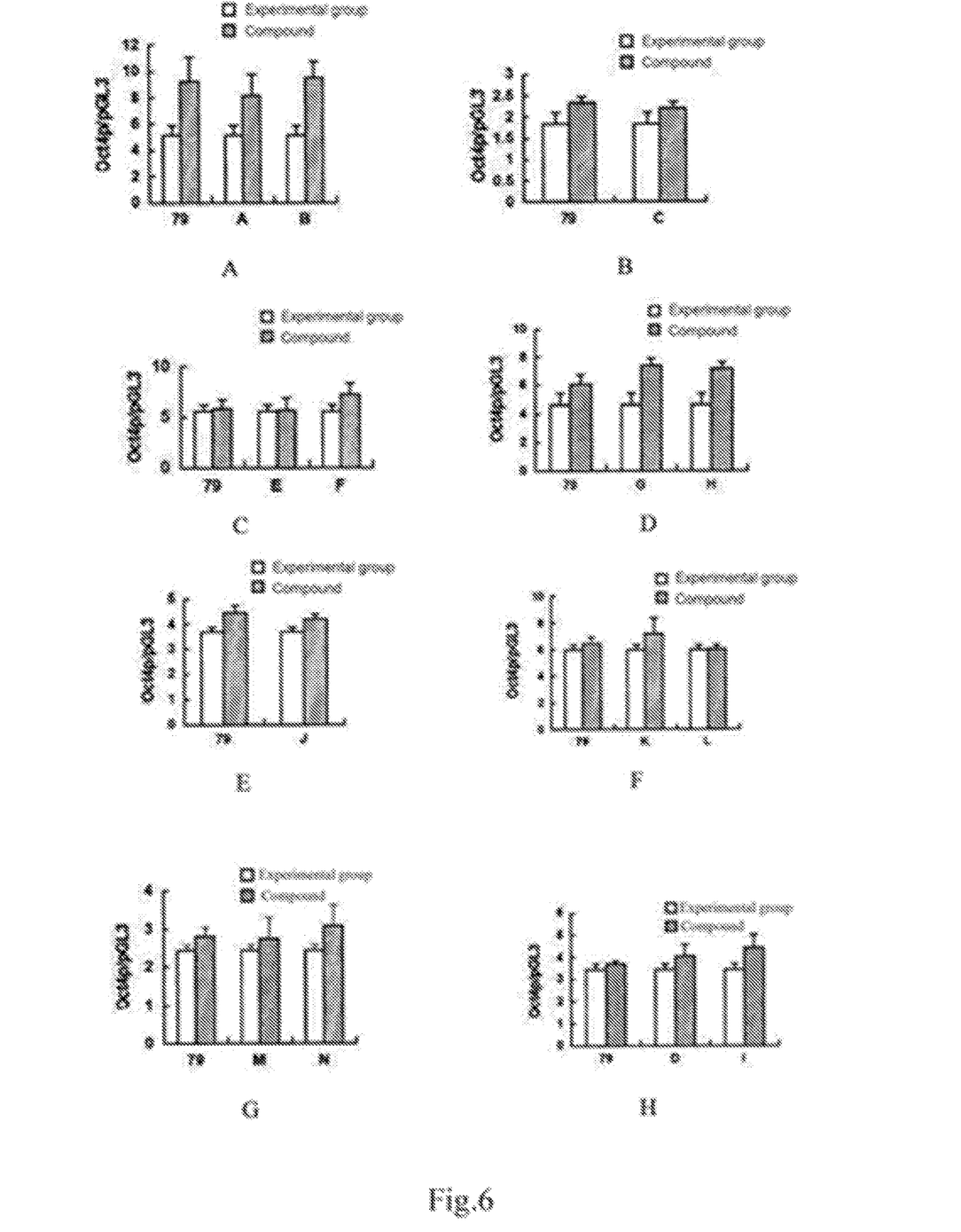
FIG. 6 shows the effect of derivatives of ethyl p-methoxycinnamate on Oct4 expression; A represents chlorogenic acid, B represents ethyl 2-cyano-3,3-diphenylacrylate, C represents ethyl indole-2-carboxylate, D represents ethyl cinnamate, E represents 4-[3-(4-methoxyphenyl)acryloyloxy]butyl-2-ynyl 3-(4-methoxyphenyl)acrylate, F represents 3-[3-(4-methoxyphenyl)acryloyloxymethyl]benzyl 3-(4-methoxyphenyl)acrylate, G represents 3-cinnamoyloxypropyl 3-propylacrylate, and H represents diethyl 4-acetoxybenzylidenemalonate.

Luciferase Reporter Assay System and FluoStar Optima were used to assay the luciferase activity of the transfected cell lysis solution. To 45 μL of the cell lysis solution was added 5 μL of Assay Cocktail reagent, after they were mixed well, 100 μL of Luciferin reaction solution was added, and fluorescence counting in 2 s was measured using FluoStar Optima instrument, which reflected the activity level of the studied plasmid reporter genes expressing firefly luciferase. To another 20 μL of the cell lysis solution was added 37.5 μL of β-gal Buffer followed by 12.5 μL of ONPG (6 mg/mL), and after they were mixed well, they were allowed to stand at 37° C. for 30 min. An absorption value at 450 nm was assayed using a microplate reader, which reflected the activity level of internal reference plasmid pCMV-β-gal expressing β-galactosidase. The ratio between the activity of the firefly luciferase and the activity of the β-galactosidase (β-gal) excluded the difference of the sample transfection efficiency, and could relatively objectively reflect the difference of promoter activity between samples. The relative luciferase activity of different samples was calculated through the following equation:

$$\text{Relative luciferase activity} = \frac{\text{Firefly luciferase activity of each sample}}{\beta\text{-galactosidase activity of each sample}}$$

Results are as shown in FIG. 6. All of the eight assayed compounds have the effect of enhancing the activity of the Oct4 promoter, wherein A represents chlorogenic acid, B represents ethyl 2-cyano-3,3-diphenylacrylate, C represents ethyl indole-2-carboxylate, D represents ethyl cinnamate, E represents 4-[3-(4-methoxyphenyl)acryloyloxy]butyl-2-ynyl 3-(4-methoxyphenyl)acrylate, F represents 3-[3-(4-methoxyphenyl)acryloyloxymethyl]benzyl 3-(4-methoxyphenyl)acrylate, G represents 3-cinnamoyloxypropyl 3-propylacrylate, and H represents diethyl 4-acetoxybenzylidenemalonate. Given all of the 8 compounds have the effect of promoting the expression of Oct4, we consider that it is the common moiety in their structures that exerts this effect, and accordingly we can speculate that other ethyl p-methoxycinnamate derivatives having this common structure, i.e. compounds having the general formula, should also have the same activity of maintaining the properties of stem cells, and can be used as regulating drugs of stem cells.

The invention claimed is:

1. A method for maintaining self-renewal and pluripotency of stem cells, comprising contacting the stem cells with an effective dosage of ethyl p-methoxycinnamate, derivatives thereof, or combinations thereof, wherein the stem cells are P19 cells, and the ethyl p-methoxycinnamate and the derivatives thereof have a structural formula wherein:
$R_1$ is 4-$OCH_3$, $R_2$ is H, $R_3$ is H, and $R_4$ is —$CH_2CH_3$;
or $R_1$ is 4-$OCH_3$, $R_2$ is H, $R_3$ is H, and $R_4$ is —$CH_2CH_2CH(CH_3)CH_3$;
or $R_1$ is 4-$OCH_3$, $R_2$ is H, $R_3$ is $COOCH_2CH_3$, and $R_4$ is —$CH_2CH_3$;
or $R_1$ is 4-$OCH_3$, $R_2$ is H, $R_3$ is $COCH_3$, and $R_4$ is —$CH_2CH_3$;

or $R_1$ is 4-OCH$_3$, $R_2$ is H, $R_3$ is CN, and $R_4$ is —CH$_2$CH$_3$;
or $R_1$ is 4-OCH$_3$, $R_2$ is CH$_3$, $R_3$ is H, and $R_4$ is —CH$_2$CH(CH$_2$CH$_3$)CH$_2$CH$_2$CH$_2$CH$_3$;
or $R_1$ is 3,4-OCH$_3$, $R_2$ is H, $R_3$ is COCH$_2$CH$_3$, $R_4$ is —CH$_2$CH$_3$;
or $R_1$ is 3,4-OCH$_3$, $R_2$ is H, $R_3$ is CN, and $R_4$ is —CH$_2$CH$_3$;
or $R_1$ is 2,4-OCH$_3$, $R_2$ is H, $R_3$ is CN, and $R_4$ is —CH$_2$CH$_3$;
or $R_1$ is 3,4,5-OCH$_3$, $R_2$ is CH$_3$, $R_3$ is H, and $R_4$ is —CH$_2$CH$_3$;
or $R_1$ is 2-OCH$_2$CH$_3$, $R_2$ is H, $R_3$ is H, and $R_4$ is —CH$_2$CH$_3$;
or $R_1$ is 4-OCH$_2$CH$_3$, $R_2$ is H, $R_3$ is H, and $R_4$ is —CH$_2$CH$_3$;
or $R_1$ is 4-OCH$_2$CH$_2$CH$_2$CH$_3$, $R_2$ is H, $R_3$ is CN, and $R_4$ is —CH$_2$CH$_3$;
or $R_1$ is 3-COOCH$_3$, $R_2$ is H, $R_3$ is H, and $R_4$ is —CH$_2$CH$_3$;
or $R_1$ is 2-CH$_3$-5-COOCH$_3$, $R_2$ is H, $R_3$ is H, and $R_4$ is —CH$_2$CH$_3$;
or $R_1$ is 4-OCOCH$_3$, $R_2$ is H, $R_3$ is COCH$_2$CH$_3$, and $R_4$ is —CH$_2$CH$_3$;
or $R_1$ is 3-OCH$_3$-4-OCH$_2$COOCH$_2$CH$_3$, $R_2$ is H, $R_3$ is H, and $R_4$ is —CH$_2$CH$_3$;
or $R_1$ is 2-OH, $R_2$ is H, $R_3$ is H, and $R_4$ is —CH$_2$CH$_3$;
or $R_1$ is 3,4-OH, $R_2$ is H, $R_3$ is H, and $R_4$ is —CH$_2$CHC(CH$_3$)CH$_3$;
or $R_1$ is 3,4-OH, $R_2$ is H, $R_3$ is H, and $R_4$ is or $R_1$ is H, $R_2$ is H, $R_3$ is H, and $R_4$ is —CH$_2$CH$_3$;
or $R_1$ is H, $R_2$ is H, $R_3$ is H, and $R_4$ is —CH(CH$_3$)CH$_3$;
or $R_1$ is H, $R_2$ is H, $R_3$ is H, and $R_4$ is —CH$_2$CH$_2$CH$_2$CH$_3$;
or $R_1$ is H, $R_2$ is H, $R_3$ is H, and $R_4$ is —CH$_2$CH(CH$_3$)CH$_3$;
or $R_1$ is H, $R_2$ is H, $R_3$ is H, and $R_4$ is —CH(CH$_3$)CH$_2$CH$_3$;
or $R_1$ is H, $R_2$ is H, $R_3$ is H, and $R_4$ is —CH$_2$CH$_2$CH(CH$_3$)CH$_3$;
or $R_1$ is H, $R_2$ is H, $R_3$ is H, and $R_4$ is —CH$_2$CH$_2$CH$_2$OOCCH=CHC$_6$H$_5$;
or $R_1$ is H, $R_2$ is H, $R_3$ is H, and $R_4$ is —CH$_2$CH$_2$C$_6$H$_5$;
or $R_1$ is H, $R_2$ is H, $R_3$ is H, and $R_4$ is —CH$_2$CH(CH$_3$)C$_6$H$_5$;
or $R_1$ is H, $R_2$ is H, $R_3$ is CN, and $R_4$ is —CH$_2$CH$_3$;
or $R_1$ is H, $R_2$ is CH$_3$, $R_3$ is H, and $R_4$ is —CH$_2$CH$_3$;
or $R_1$ is H, $R_2$ is C$_6$H$_5$, $R_3$ is CN, and $R_4$ is —CH$_2$CH$_3$;
or $R_1$ is 2,6-C$_1$, $R_2$ is H, $R_3$ is H, and $R_4$ is —CH$_2$CH$_3$;
or $R_1$ is 4-Br, $R_2$ is H, $R_3$ is H, and $R_4$ is —CH$_2$CH$_3$;
or $R_1$ is 2-CF$_3$, $R_2$ is H, $R_3$ is H, and $R_4$ is —CH$_2$CH$_3$;
or $R_1$ is 2-OH-4-Br, $R_2$ is H, $R_3$ is H, and $R_4$ is —CH$_2$CH$_3$;
or $R_1$ is 4-Cl, $R_2$ is H, $R_3$ is COOCH$_2$CH$_3$, and $R_4$ is —CH$_2$CH$_3$;
or $R_1$ is 4-Cl, $R_2$ is H, $R_3$ is OCH$_2$CH$_3$, and $R_4$ is —CH$_2$CH$_3$;
or $R_1$ is 3,4-F, $R_2$ is H, $R_3$ is OCH$_2$CH$_3$, and $R_4$ is —CH$_2$CH$_3$;
or $R_1$ is 2-Cl-4-F, $R_2$ is H, $R_3$ is CN, and $R_4$ is —CH$_2$CH$_3$;
or $R_1$ is 3-Cl-4-OCH$_3$, $R_2$ is H, $R_3$ is CN, and $R_4$ is —CH$_2$CH$_3$;
or $R_1$ is 2-Cl-4-OCH$_3$, $R_2$ is H, $R_3$ is CN, and $R_4$ is —CH$_2$CH$_3$;
or $R_1$ is 4-NH$_2$, $R_2$ is H, $R_3$ is H, and $R_4$ is —CH$_2$CH$_3$;
or $R_1$ is 3-CN, $R_2$ is H, $R_3$ is H, and $R_4$ is —CH$_2$CH$_3$;
or $R_1$ is 4-NO$_2$, $R_2$ is H, $R_3$ is H, and $R_4$ is —CH$_2$CH$_3$;
or $R_1$ is 4-(2,4-F—C$_6$H$_4$), $R_2$ is CH$_3$, $R_3$ is H, and $R_4$ is —CH$_2$CH$_3$;
or $R_1$ is 4-OCH$_3$, $R_2$ is H, $R_3$ is H, and $R_4$ is —CH$_2$—C$_6$H$_4$—CH$_2$—OOC—CH=CH—C$_6$H$_4$-β-CH$_3$;
or $R_1$ is 4-OCH$_3$, $R_2$ is H, $R_3$ is H, and $R_4$ is —CH$_2$—C—CH$_2$—OOC—CH=CH—C$_6$H$_4$-β-CH$_3$;
or $R_1$, $R_2$ and $R_3$ form a heterocyclic structure and $R_4$ is —CH$_2$CH$_3$;
or $R_1$, $R_2$ and $R_3$ form a heterocyclic structure and $R_4$ is —CH$_2$CH$_3$;
or $R_1$, $R_2$ and $R_3$ form a heterocyclic structure and $R_4$ is —CH$_2$CH$_3$;
or $R_1$, $R_2$, $R_3$ form a heterocyclic structure and $R_4$ is —CH$_2$CH$_3$;
or $R_1$ is —N—CH$_3$(CH$_3$), $R_2$ is H, and $R_3$ and $R_4$ form a heterocyclic structure 2. The method according to claim 1, wherein the derivatives thereof are selected from iso-pentyl methoxycinnamate, diethyl 4-methoxybenzalmalonate, ethyl 2-(4-methoxybenzylidene)acetoacetate, ethyl 2-cyano-3-(4-hydroxyethylphenyl)acrylate, octyl 4-methoxycinnamate, diethyl 2-(3,4-dimethoxybenzylidene)malonate, ethyl 2-cyano-3-(3,4-dimethoxyphenyl)-2-butenoate, ethyl trans-2-cyano-3-(2,4-dimethoxyphenyl)-2-acrylate, ethyl trans-3-(3,4,5-trimethoxyphenyl)-2-crotonate, ethyl 2-hydroxyethylcinnamate, ethyl trans-4-ethoxycinnamate, ethyl 3-(4-butoxyphenyl)-2-cyanoacrylate, methyl 3-(trans-3-hydroxyethyl-3-oxo-1-propenyl)benzoate, methyl 3-(trans-3-ethoxy-3-oxo-1-propenyl)-4-methylbenzoate, diethyl 4-acetoxybenzylidenemalonate, ethyl 3-(3-methoxy-4-methoxycarbonylmethoxyphenyl)acrylate, ethyl trans-2-hydroxycinnamate, caffeic acid-1,1-dimethylacrylate, neochlorogenic acid, ethyl cinnamate, iso-propyl cinnamate, butyl cinnamate, iso-butyl cinnamate, propyl 3-methylcinnamate, iso-pentyl cinnamate, 3-cinnamoyloxypropyl 3-propylacrylate, phenylethyl cinnamate, 3-phenylpropyl cinnamate, ethyl trans-2-cyanocinnamate, ethyl trans-β-methylcinnamate, ethyl 2-cyano-3,3-diphenylacrylate, ethyl 2,6-dichlorocinnamate, ethyl trans-4-bromo cinnamate, ethyl trans-3-(2-trifluoromethylphenyl)-2-acrylate, ethyl trans-3-(4-bromo-2-hydroxyphenyl)-2-acrylate, diethyl 4-chlorobenzylidenemalonate, ethyl cis-3-(4-chlorophenyl)-2-hydroxyethyl-2-acrylate, ethyl cis-3-(3,4-difluorophenyl)-2-ethoxy-2-acrylate, ethyl 3-(2-chloro-4-fluorophenyl)-2-cyano-2-acrylate, ethyl 3-(3-chloro-4-methoxyphenyl)-2-cyanoacrylate, ethyl 3-(2-chloro-4-methoxyphenyl)-2-cyanoacrylate, ethyl 4-aminocinnamate, ethyl 3-cyanocinnamate, ethyl 4-nitrocinnamate, 3-[2,4-difluoro (1,1-biphenyl)-4-yl]-2-butenoate, 3-[3-(4-methoxyphenyl) acryloyloxymethyl]benzyl 3-(4-methoxyphenyl)acrylate, 4-[3-(4-methoxyphenyl)acryloyloxy]butyl-2-ynyl 3-(4-methoxyphenyl)acrylate, ethyl indole-2-carboxylate, ethyl 6-methoxy-1-benzofuran-2-carboxylate, ethyl 6-amino-3-methyl-1-benzofuran-2-carboxylate, ethyl 5-methylindole-2-carboxylate, or trans-3-(4-dimethylaminobenzylidene)dihydro-2(3H)-furanone.

3. The method according to claim 1, wherein the ethyl p-methoxycinnamate and the derivatives thereof promote expression of Oct4 genes.

4. The method according to claim 1, wherein the effective dosage is 0.01-100 mg/kg.

5. The method according to claim 1, wherein the method is used for in in-vitro preparation of stem cells.

6. The method according to claim 1, wherein the method is used for in-vitro amplification of stem cells.

\* \* \* \* \*

```
                         SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ctcgaaccac atccttctct                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
tcgtgcgtga cattaaggag                                              20
```